United States Patent [19]

Codrington

[11] Patent Number: 4,572,198
[45] Date of Patent: Feb. 25, 1986

[54] CATHETER FOR USE WITH NMR IMAGING SYSTEMS

[75] Inventor: Robert S. Codrington, Los Altos Hills, Calif.

[73] Assignee: Varian Associates, Inc., Palo Alto, Calif.

[21] Appl. No.: 621,635

[22] Filed: Jun. 18, 1984

[51] Int. Cl.⁴ .............................................. A61B 5/05
[52] U.S. Cl. ...................................... 128/653; 128/658
[58] Field of Search ................................ 128/653–658

[56] References Cited

U.S. PATENT DOCUMENTS

| | | | |
|---|---|---|---|
| 3,847,157 | 11/1974 | Caillouette et al. | 128/656 |
| 4,254,778 | 3/1981 | Clow et al. | 128/653 |
| 4,431,005 | 2/1984 | McCormick | 128/653 |
| 4,445,501 | 5/1984 | Bresler | 128/1.5 |
| 4,459,990 | 7/1984 | Barnea | 128/656 |

Primary Examiner—Kyle L. Howell
Assistant Examiner—Ruth S. Smith
Attorney, Agent, or Firm—Stanley Z. Cole; Edward H. Berkowitz

[57] ABSTRACT

A magnetic resonance catheter system combining with a magnetic resonance imaging device, a catheter including a coil winding for exciting a weak magnetic field at the tip of the catheter. The location of the catheter tip is thereby obtained in cooperation with the magnetic resonance imager.

3 Claims, 4 Drawing Figures

U.S. Patent    Feb. 25, 1986    4,572,198
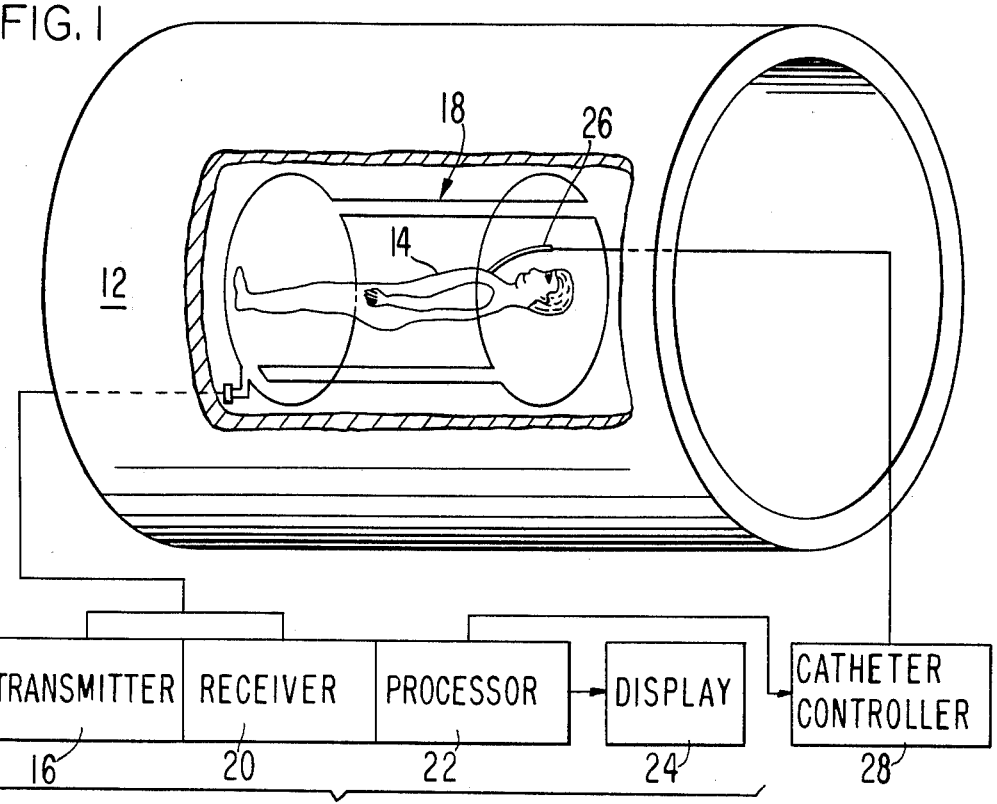
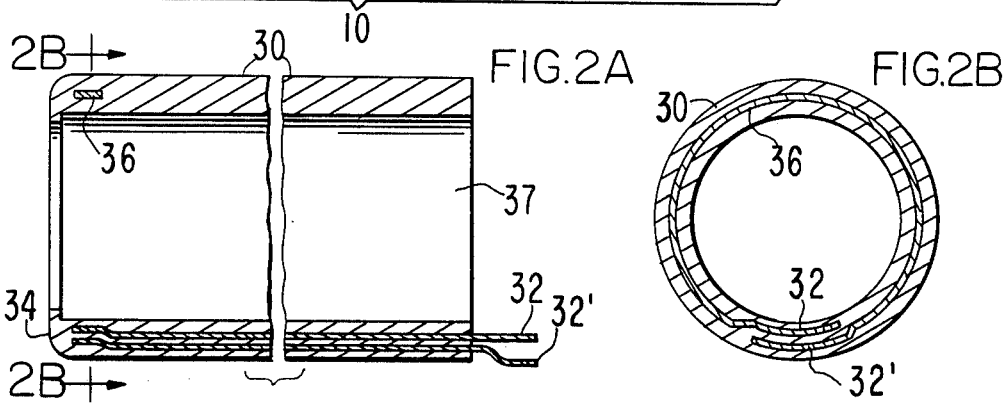
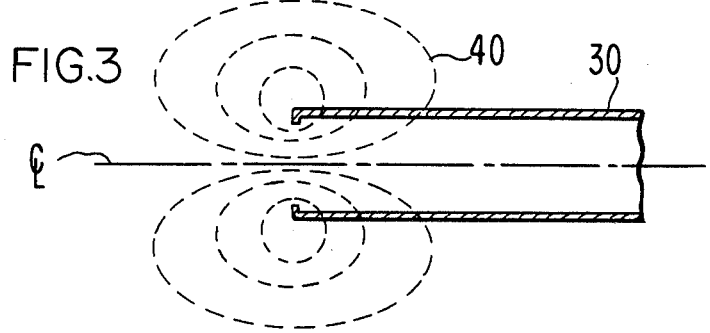

CATHETER FOR USE WITH NMR IMAGING SYSTEMS

FIELD OF THE INVENTION

The present invention is in the field of medical magnetic resonance imaging and relates to catheter apparatus for use with magnetic resonance imaging.

BACKGROUND OF THE INVENTION

Catherization procedures have been refined for a variety of in vivo sensing techniques. In conjunction with imaging means, catheter apparatus may be precisely located to accomplish the special procedure for which the catheter is to be employed.

In nuclear magnetic resonance (NMR) imaging, the spatial density distribution of coherent nuclear magnetization (usually that of hydrogen nuclei) is mapped and the sensitivity of the scanning apparatus to hydrogenous materials forms the basis for recording the progress of the catheter if the latter is substantially more visible in the imaging apparatus than its surroundings. If the structural portions of the catheter are simply more hydrogenous than the tissue surrounding, the catheter is detectable but a limit is placed on the available contrast. Additionally, tissue in the near environs of the catheter may be obscured. Moreover, most catheters comprise functional elements such as light pipes, cutting devices, electrode wires and the like contained within a semi-rigid sheath made of materials chemically inert to body fluids. These functional elements tend to degrade the magnetic resonance imaging and cause a loss of resolution which in turn renders more uncertain the critical location of the catheter terminus. The present invention overcomes the NMR contrast limitation through provision of a localized and controllable magnetic field source at the catheter tip, whereby the location of the tip is unequivocally determined in an NMR image.

BRIEF SUMMARY OF THE INVENTION

The present invention is implemented with a strip line comprising a pair of adjacent foil conductors embedded in the catheter sheath material and electrically terminating in a loop at the catheter tip. The conductors are constructed to exhibit a magnetic susceptibility substantially matched to that of the sheath. A weak dipole field is excited by current pulses during alternate imaging intervals resulting in local degradation of the NMR image during these alternate imaging intervals. Adjacent imaging intervals are then combined in a subtractive mode to precisely locate the loop of the catheter tip.

BRIEF DESCRIPTION OF THE FIGURES

FIG. 1 is a block diagram of a system according to the present invention.

FIG. 2A is a longitudinal section of a portion of the catheter of the present invention.

FIG. 2B is a transverse section of a portion of the catheter near the tip thereof.

FIG. 3 is a schematic picture of the field of the NMR catheter is use.

DETAILED DESCRIPTION OF THE PRESENT INVENTION

FIG. 1 is a block diagram of the present invention. Imaging apparatus 10 is any one of a number of magnetic resonance imaging systems. Such systems exhibit a two, or three dimensional spatial sensitivity to the distribution of a specified magnetic moment. The specific system is not critical: it is only essential that an image is formed of the region of interest. Imaging apparatus 10 comprises a magnet system 12 for imposing a magnetic field distribution H (x, y, z, t) on subject 14 and a rotating magnetic field obtained from RF energy source 16 through RF coil structures 18. Receiver 20 responds to the resonance signal and image processor 22 reconstitutes a spatial function f (x, y, z) from which a desired projection, e.g., $f_z$ (x, y) is graphically realized by display device 24. A catheter 26 of the present invention together with catheter control 28 is more fully discussed below.

Turning now to FIGS. 2 there is shown a longitudinal section of the portion of a catheter structure. The sheath 30 is preferably constructed of a reinforced fluoroplastic characterized by good insulating and dielectric properties and a relatively low magnetic susceptibility. One material appropriate for the purpose is Teflon or Kelf.

The sheath 30 has embedded within the wall thereof a pair of conductors 32 and 32'. These are preferably formed of a foil composite obtained by plating or other deposition technique of conductive materials of selected magnetic susceptibility to yield a composite of desired susceptibility substantially matching that of the sheath. Techniques for matching susceptibility are discussed in U.S. Ser. No. 482,344. In this way the magnetic invisibility of the catheter is maintained.

The foil conductors are separated by a distance which is short compared to the other dimensions of the conductors and forms a strip line. Pulse propagation over a strip line is substantially confined to the region bounded thereby and the stray fields external to this region effectively cancel.

The tip 34 of the catheter contains a loop 36 connecting the conductors 32 and 32'. The plane of the loop is preferably transverse to the catheter symmetry axis 37. When excited by a weak pulse source, the loop supports a dipole magnetic field 40 as in FIG. 3 which locally distorts the NMR image providing an image cursor on the magnetic resonance imaging display. It is preferably to utilize a weak excitation in order that the cursor is minimal in spatial extent.

The principal purpose of the invention is the accurate location and monitoring of the catheter tip. A low magnetic susceptibility functional element, light pipe or the like, is threaded into the catheter sheath and the catheter is directed through the selected blood vessels toward the situs of investigation. During this positioning operation, the excitation of the catheter loop is alternately on and off during sequentially adjacent NMR image acquisitions. This is accomplished by catheter controller 28. The image acquisition occupies an interval of the order of a few seconds and pairs of consecutive images are preferably compared in a subtractive mode by processor 22 to emphasize the location of the catheter tip. Synchronization of the catheter controller 28 and processor 22 is straightforward. Preferably, processor 22 provides a signal concurrent with alternate consecutive images to activate the weak magnetic field 40 at the catheter tip. The subtractive mode image information defines an image cursor which is preferably superimposed on the additive display of the same images or even of the most recent single image. Having thus positioned the catheter tip, the low susceptibility functional element may be removed and the desired elements inserted in the catheter sheath. It is assumed that such other elements are conductive or exhibit a high magnetic susceptibility which would otherwise adversely affect the NMR image during the positioning steps of the operation.

The use of the pulsing field from the catheter tip can be speeded up by limiting the calculation of the image to a limited number of pixels in the immediate area of the catheter tip. This technique is preferably coupled with a suitable algorithm to keep this "zoomed" image centered on the tip of the catheter. A CRT display then provides a quasi-real time picture of the catheter moving through the body. In a preferred display mode, the operator sees the tip of the catheter as a flashing intensity or contrasting color which can be controlled by the gray, or color scale selected to maximize the resolution of the NMR signals in the region of the pixels displayed.

What is claimed is:

1. In combination, a magnetic resonance imaging system for obtaining the spatial distribution of a selected magnetic parameter characterizing tissue constituents of a subject and a catheter for insertion into said subject, said catheter comprising means for controllably disturbing the magnetic field in the vicinity of a local portion of said catheter and thereby interacting with said magnetic resonance imaging system.

2. The combination of claim 1, said catheter and comprising:
   a hollow sheath comprising a flexible elongate insulator, and
   said means for controllably disturbing comprising a pair of conductive strips imbedded in said insulator and extending substantially the length thereof,
   conductive loop means imbedded in said sheath and disposed proximate to one end thereof, said loop mutually connecting said conductive strips, and excitation means for applying a selectable current through said conducting strips and thence through said loop whereby a controllable dipole magnetic field is achieved in the vicinity thereof.

3. The method of investigating the spatial relationship of a catheter within a body to organs of said body comprising:
   introducing said catheter into said body, exciting a weak magnetic field at the terminus of said catheter, and
   forming a magnetic resonance image of said body whereby said magnetic resonance image is locally perturbed in the neighborhood of said weak magnetic field and the location of said catheter in relation to said organs is determined.

* * * * *